United States Patent [19]

Malinow

[11] Patent Number: 4,602,003
[45] Date of Patent: Jul. 22, 1986

[54] SYNTHETIC COMPOUNDS TO INHIBIT INTESTINAL ABSORPTION OF CHOLESTEROL IN THE TREATMENT OF HYPERCHOLESTEROLEMIA

[75] Inventor: M. René Malinow, Portland, Oreg.

[73] Assignee: Medical Research Foundation of Oregon, Portland, Oreg.

[21] Appl. No.: 379,098

[22] Filed: May 17, 1982

[51] Int. Cl.$^4$ ............... A01N 31/00; A61K 31/705; A61K 31/58; A61K 31/56
[52] U.S. Cl. ..................... 514/26; 536/5; 260/239.55 A; 260/397.2; 514/172; 514/169
[58] Field of Search ............. 260/239.55 A, 397.2; 563/6, 6.1; 424/238, 180

[56] References Cited

U.S. PATENT DOCUMENTS

| | | | |
|---|---|---|---|
| 3,160,626 | 12/1964 | Oxley | 260/239.55 A |
| 3,303,187 | 2/1967 | Rubin | 260/239.55 A |
| 3,992,315 | 11/1976 | Dibb et al. | 536/5 |
| 4,188,379 | 2/1980 | Pegel | 424/182 |
| 4,198,401 | 4/1980 | Pegel | 424/195 |
| 4,242,502 | 12/1980 | Malinow et al. | 424/182 |
| 4,254,111 | 3/1981 | Pegel et al. | 424/182 |
| 4,260,603 | 4/1981 | Pegel et al. | 424/182 |
| 4,265,886 | 5/1981 | Pegel | 424/182 |

FOREIGN PATENT DOCUMENTS 2425859 12/1977 France.

OTHER PUBLICATIONS

Kintya et al., "Search for Hypochotesferemic Agents Among a Group of Steroid Glycosides", Kim. Farm. Zh (1981) 15:9, pp. 56–60.
M. R. Malinow, et al., "Prevention of Hypercholesterolemia in Monkeys (Macaca fascicularis) by Digitonin", Am. J. Clin. Nut. 31:814–818 (1978).
R. J. Morris, et al., "Isolation, Purification, and Structural Identity of an Alfalfa Root Saponin", J. Org. Chem., 26:1241–1243 (1961).
Anderson, "Effect of Alfalfa Saponin on the Performance of Chicks and Laying Hens", Chem. Abs. 52:2194f (1958).
Bite et al., "Synthesis of Steroid Glycosides", Chem. Abs. 66:38204v (1967).
Cayen et al., "Effect of Diosgenin on Lipid Metabolism in Rats", J. Lipid Research 20:162–173 (1979).
Griminger et al., "Dietary Saponin and Plasma Cholesterol in the Chicken", Proc. Soc. Exp. Biol. Med., 99:424–426 (1958).
Ishaaya et al., "Soybean Saponins, IX., Studies of Their Effect on Birds, Mammals and Cold–Blooded Organisms", J. Sci. Fd. Agric. 20:433–436 (1969).
Malinow et al., "Effect of Alfalfa Saponins on Intestinal Cholesterol Absorption in Rats", Am. J. Clin. Nutr. 30:2061–2067 (1977).
Malinow et al., "Cholesterol and Bile Acid Balance in Macaca fascicularis", J. Clin. Invest. 67:156–162 (1981).
Morgan et al., "The Interactions Between Dietary Saponin, Cholesterol and Related Sterols in the Chick", Poultry Sci. 51:677–682 (1972).
Newman et al., "Dietary Saponin, A Factor Which May Reduce Liver and Serum Cholesterol Levels", Poultry Sci. 37:42–46 (1958).
Oakenfull, "Effects of Saponins on Bile Acids and Plasma Lipids in the Rat", Br. J. Nutr. 42:209–216 (1979).
Reshef et al., "Effect of Alfalfa Saponins on the Growth and Some Aspects of Lipid Metabolism of Mice and Quails", J. Sci. Fd. Agric. 27:63–72 (1976).
Segal et al., "Hemolytic Properties of Synthetic Glycosides", Biol. Abs. 67:57966 (1979).
Sofowora et al., "Synthesis of 3-β-Glycosides of Diosgenin, Yamogenin and Gitogenin", Biol. Abs. 63:4467 (1977).
Topping et al., "Effects of Dietary Saponins on Fecal Bile Acids and Neutral Sterols, Plasma Lipids, and Lipoprotein Turnover in the Pig", Am. J. Clin. Nutr. 33:783–786 (1980).
Topping et al., "Prevention of Dietary Hypercholesterolemia in the Rat by Soy Flour High and Low in Saponins", Nutr. R. Intl. 22:513–519 (1980).
Wilcox et al., "Serum and Liver Cholesterol, Total Lipids and Lipid Phosphorus Levels of Rats Under Various Dietary Regimens", Am. J. Clin. Nutr. 9:236–243 (1961).
Merck Index (1976), pp. 439 and 1217.
"Steroids" by Fieser et al (1959), p. 28.

Primary Examiner—Elbert L. Roberts
Attorney, Agent, or Firm—Klarquist, Sparkman, Campbell, Leigh & Whinston

[57] ABSTRACT

Synthetic sapogenin and sterol compounds, administered orally to warm-blooded animals, inhibit the absorption of cholesterol and are useful in the treatment of hypercholesterolemia. Particular compounds suitable for such purposes include glycosides with spirostane, spirostene, or cholesterol aglycones, and esters of spirostanes, spirostenes and cholesterol.

15 Claims, No Drawings ial absorption of cholesterol, and prevents the hypercholesterolemia expected in monkeys ingesting high-fat, highcholesterol foods (M. R. Malinow, et al, "Prevention of Hypercholesterolemia in Monkeys (*Macaca fascicularis*) by Digitonin, *Am. J. Clin. Nutr.*, 31:814–818, 1978). But, digitonin is costly. Diosgenin has also been reported to inhibit the absorption of cholesterol in rats when given in a massive dose (1000 mg/kg) (M. N. Cayen, et al., "Effect of Diosgenin on Lipid Metabolism in Rats.", *J. Lipid Res.* 20: 162-174, 1979).

SYNTHETIC COMPOUNDS TO INHIBIT INTESTINAL ABSORPTION OF CHOLESTEROL IN THE TREATMENT OF HYPERCHOLESTEROLEMIA

This invention was made with government support under Grant No. 5 P51 RR00163 "Support for Regional Primate Research Center" awarded by the Department of Health and Human Services, Division of Research Resources. The government has certain rights in this invention.

BRIEF SUMMARY OF THE INVENTION

The invention relates to synthetic compounds which, when administered orally to warm-blooded animals, inhibit the absorption of cholesterol.

Certain water/alcohol soluble extracts from plant sources have been found to reduce cholesterolemia in chicks, pigs and rats (P. Griminger, et al., "Dietary Saponin and Plasma Cholesterol in the Chick." *Proc. Soc. Exp. Biol. Med.* 99:424-426, 1958; H. A. I. Newman, et al. "Dietary Saponins, a Factor Which May Reduce Liver and Serum Cholesterol Levels." *Poultry Sci.* 37:42-46, 1958; B. Morgan, et al., "The Interactions Between Dietary Saponin, Cholesterol and Related Sterols in the Chick." *Poultry Sci.* 51:677-682, 1972; D. L. Topping, et al, "Effects of Dietary Saponins in Fecal Bile Acids and Neutral Sterols, Plasma Lipids, and Lipoprotein Turnover in the Pig." *Am. J. Clin. Nutr.* 33:783-786, 1980; D. G. Oakenfull, et al., "Effects of Saponins on Bile-acids and Plasma Lipids in the Rat." *Br. J. Nutr.* 42:209-216, 1979; and D. L. Topping, et al., "Prevention of Dietary Hypercholesterolemia in the Rat by Soy Flour High and Low in Saponins." *Nutr. Rep. Int.* 22:513-519, 1980.)

More specifically, extracts from alfalfa hay are known to be active in reducing the absorption of dietary cholesterol. Although such alfalfa extracts are of unknown composition, they are found to contain saponins identifiable by thin-layer chromatography. The alfalfa extracts contain, in addition to saponins, unspecified amounts of carbohydrates, amino acids, peptides, pigments, and free aglycones removed from alfalfa hay by the water:alcohol solvent used during their preparation. Such crude extracts are sometimes referred to herein as "alfalfa saponins" as an operational definition. These alfalfa extracts reduce the intestinal absorption of cholesterol in rats and monkeys (M. R. Malinow, et al., "Cholesterol and Bile Acid Balance in *Macaca fascicularis:* Effects of Alfalfa Saponins." *J. Clin. Invest.* 67:156-162, 1981). The capacity of such alfalfa extracts to interfere with cholesterol absorption is enhanced by partial acid hydrolysis as reported in M. R. Malinow, et al., "Effect of Alfalfa Saponins on Intestinal Cholesterol Absorption in Rats." *Am. J. Clin. Nutr.* 30:2061-2067, 1977; and U.S. Pat. No. 4,242,502 (Malinow, et al.)).

Digitonin binds cholesterol in vitro, inhibits the intestinal absorption of cholesterol, and prevents the hypercholesterolemia expected in monkeys ingesting high-fat, highcholesterol foods (M. R. Malinow, et al, "Prevention of Hypercholesterolemia in Monkeys (*Macaca fascicularis*) by Digitonin, *Am. J. Clin. Nutr.*, 31:814–818, 1978). But, digitonin is costly. Diosgenin has also been reported to inhibit the absorption of cholesterol in rats when given in a massive dose (1000 mg/kg) (M. N. Cayen, et al., "Effect of Diosgenin on Lipid Metabolism in Rats.", *J. Lipid Res.* 20: 162-174, 1979).

It was previously reported that toxicity of plant saponins is decreased in rats, mice, and birds by cholesterol in the diet (J. O. Anderson, "Effect of Alfalfa Saponin on the Performance of Chicks and Laying Hens." *Poult. Sci.* 36:873-876, 1957; I. Ishaaya, et al., "Soyabean Saponins. IX. Studies of Their Effects on Birds, Mammals and Cold-blooded Organisms." *J. Sci. Food Agric.,* 20:433-436, 1969; G. Reshef, et al., "Effect of Alfalfa Saponins on the Growth and Some Aspects of Lipid Metabolism of Mice and Quails." *J. Sci. Food Agric.* 27:63-72, 1976; E. B. Wilcox, et al., "Serum and Liver Cholesterol, Total Lipids and Lipid Phosphorus Levels of Rats Under Various Dietary Regimes." *Am. J. Clin. Nutr.,* 9:236-243, 1961).

Despite these encouraging results, it has remained a problem that plant extracts, which are of variable composition, contain a volume of nonuseful chemical substances. It is difficult, due to the variations in composition, to set a standard dosage or predict the impurities present. Thus, such extracts are not well suited for use by humans. Furthermore, purification of plant extract substances and synthesis of saponins suspected to exist in plants are likely to be very costly due to the anticipated complexity of the required procedures.

It has now been discovered that certain synthetically produced, pure "sapogenin-derived" compounds, e.g., substances compounded from spirostane, spirostene, or sterol-derived" compounds are nontoxic. Such compounds depress cholesterol absorption more effectively than alfalfa extracts on a weight basis and thus can be administered in reasonably sized doses. Because the chemical compositions of these substances are known and because they can be synthesized at a high degree of purity, they are suitable for use by any warm-blooded animal, including humans. Precursor substances for use in the synthesis are available as by-products of present industrial processes. For example, one spirostane compound (tigogenin) is currently a wasted by-product of digitalis manufacture.

Unless administered in massive amounts, pure sapogenins do not significantly bind cholesterol or inhibit its absorption. It is only when compounded with another moiety that sapogenins have the desired effect. Examples of such sapogenin compounds are compounds of tigogenin and diosgenin, particularly glycosides having tigogenin or diosgenin as an aglycone. Although it is not established that the size of the nonsapogenin moiety has any effect on a compound's ability to inhibit cholesterol absorption, at least one glycoside with a relatively longer sugar moiety has an increased biological activity in regard to cholesterol absorption. Specifically, cellobiose-sapogenins are more active than glucose-sapogenins having the same aglycone. Of such substances, cellobiose-tigogenin is particularly active to inhibit cholesterol absorption. Somewhat less active is cellobiose-diosgenin, perhaps due to the presence of a double bond in $C_5$ of the spirostene aglycone of diosgenin.

DETAILED DESCRIPTION

Certain synthetic compounds, when administered orally, inhibit the absorption of cholesterol by warm-blooded animals, and consequently may lower plasma cholesterol levels and induce regression of atherosclerosis. These include compounds of sterols and of "spirostane substances" such as diosgenin, tigogenin, smilagenin and the like. One group of such compounds includes compounds of diosgenin (5,20α,22α,25d-spirostan-3β-ol) as represented by the following formula:

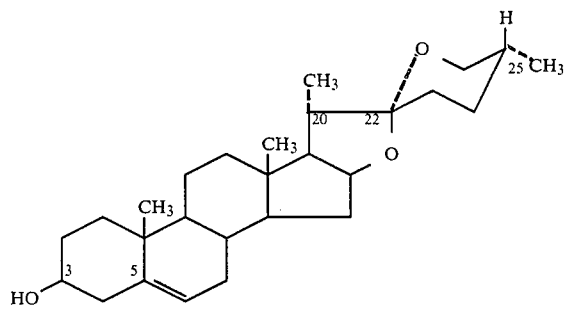

Another group according to the invention include compounds of tigogenin (5α,20α,22α,25D-spirostan-3β-ol) represented by formula:

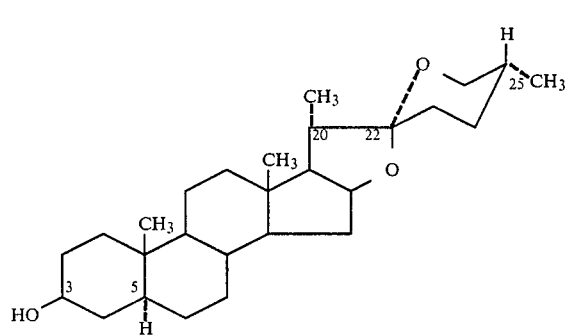

A. Esters

Esters of the above formulas can be prepared by reacting an anhydride with the "spirostane substance". Any of numerous organic anhydride substances could be used in such molecules, although not all such molecules would be effective or be sufficiently nontoxic for general use.

Esters have been formed from the following anhydrides which react with the hydroxyl group of the sapogenin or sterol:

| Anhydrides Used in the Synthesis of Sapogenin and Sterol Esters | |
| --- | --- |
| phtalyl-DL-glutamic | cis-1,2-cyclobutane dicarboxylic |
| 1-octenyl-succinic | citraronic |
| glutaric | 3-nitrophtalic |
| nonenylsuccinic | methylsuccinic |
| trans-1,2-cyclohexane dicarboxylic | 3-methylglutaric |
| cix-1,2-cyclohexanedicarboxylic | 2,3-dimethyl maleic |
| 3,3-dimethyl glutaric | 1,2,3,4-cyclobutane tetracarboxylic |
| trans-1,2-cyclohexanedi-carboxylic | diphenyl |
| 2-dodecen-1-ylsuccinic | maleic |
| dichloromaleic | |

Of the esters produced, only maleic esters proved to be effective in the inhibition of intestinal absorption of cholesterol in laboratory animals.

Such maleic esters were synthesized by combining maleic anydride and the desired sapogenin or sterol substance in chloroform at 50° for a period of four days. The result was a maleic ester of the formula:

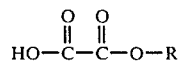

wherein R is a sapogenin such as diosgenin or tigogenin or a sterol such as cholesterol.

Tests were performed on laboratory animals according to the procedure outlined in M. R. Malinow, et al., "Effect of Alfalfa Saponins on Intestinal Cholesterol Absorption in Rats." Am. J. Clin. Nutr., 30, December 1977, pps. 2061–2067. The tests were performed in groups of six animals each (mean±SE). The result of the tests are summarized in Table I:

TABLE I

Effect of Sapogenin Esters on Intestinal Absorption of Cholesterol in Rats. Tests performed in groups of six animals each (mean ± SE)

| Substance | mg/rat | Intestinal absorption of cholesterol (% of I.D.) | | P |
| --- | --- | --- | --- | --- |
| | | Controls | Experimental | |
| tigogenin maleate | 15 | 80.5 ± 0.6 | 62.9 ± 1.0 | 0.001 |
| diosgenin maleate | 15 | 79.6 ± 1.4 | 56.0 ± 2.2 | 0.001 |
| tigogenin | 15 | 79.1 ± 1.5 | 81.2 ± 1.1 | N.S. |
| diosgenin | 15 | 73.5 ± 2.0 | 76.4 ± 2.6 | N.S. |
| maleic acid | 15 | 79.1 ± 1.5 | 78.1 ± 0.8 | N.S. |
| maleic acid/tigogenin | 5/10 | 77.0 ± 2.1 | 78.1 ± 0.8 | N.S. |
| Maleic acid/diosgenin | 5/10 | 77.0 ± 2.1 | 71.2 ± 2.8 | N.S. |

In vitro tests for micellar cholesterol binding were performed according to the method of M. R. Malinow, et al., "Prevention of Hypercholesterolemia in Monkeys (Macaca fascicularis) by Digitonin." Am. J. Clin. Nutr. 31:814–818, 1978. These tests confirmed that cholesterol was bound by the sapogenin maleates. The results of these in vitro tests appear in Table II:

TABLE II

| In Vitro Micellar Cholesterol Binding | |
| --- | --- |
| Substance | Bound cholesterol (mg/mg substance) |
| Tigogenin maleate | 0.20 |
| diosgenin maleate | 0.24 |
| digitonin | 0.33 |
| alfalfa saponins | 0.24 |
| tigogenin | 0 |
| diosgenin | 0 |

When tested in primates, however, the sapongenin maleates induced vomiting when administered orally. Thus, the maleates may be unacceptable for administration to humans, or even be toxic.

B. Glycosides

Sapogenin and sterol compounds according to the invention, specifically glycosides of tigogenin, diosgenin and cholesterol successfully bind cholesterol and inhibit its absorption by the digestive system of warm-blooded animals. Thus far, no toxic effect has been associated with such substances. And, due to their structure, it is likely that they are substantially nontoxic.

The glucosidic compounds were formed by reacting a carbohydrate-containing molecule with the hydroxyl group of the aglycone substance. The carbohydrate-containing molecule can, for example, be α-D-(+)-glucose of the formula:

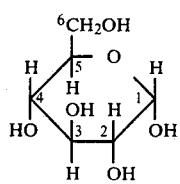

or β-D-(+)-glucose of the formula:

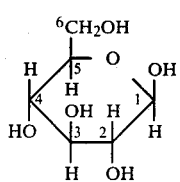

or longer carbohydrate molecules such as (+)-cellobiose(β-anomer) otherwise known as 4-O-(β-D-glucopyranosyl-D-glucopyranose):

The glycosidic bonds between the carbohydrate-containing molecule and the aglycone could be either an α glycosidic bond:

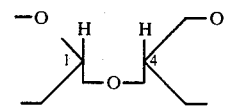

or a β glycosidic bond:

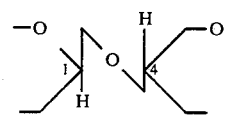

For compounds which are to bind cholesterol, it is anticipated that a β glycosidic bond will be preferred in most instances since compounds having a β glycosidic bond are less likely to be hydrolyzed in the intestine of the subject animal.

Thus, although an α-cellobiose-tigogenin of the following formula might be suitable,

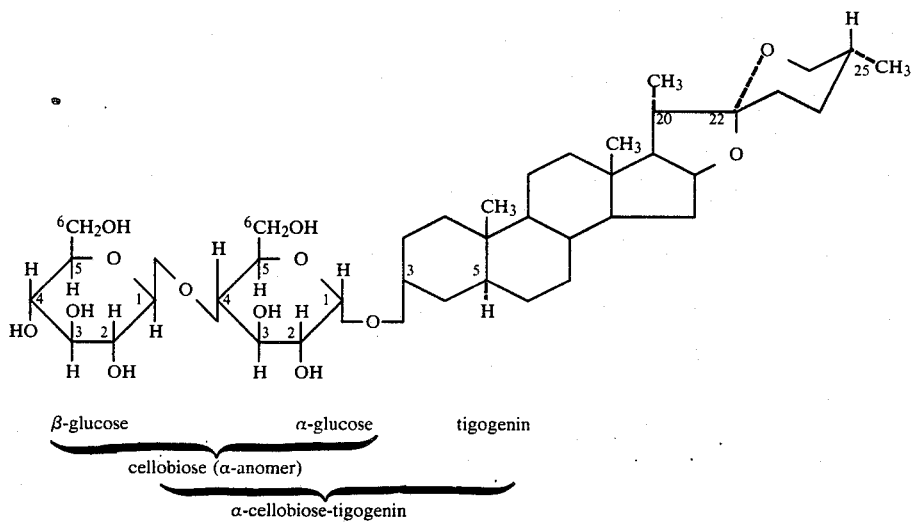

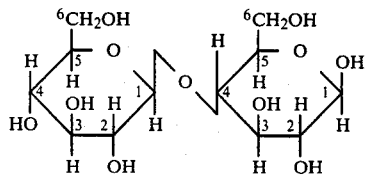

it is anticipated that a β-cellobiose-tigogenin, such as one of the following formula, would be more effective:

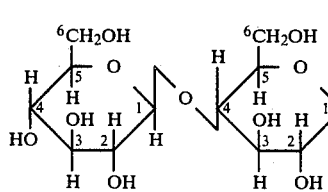

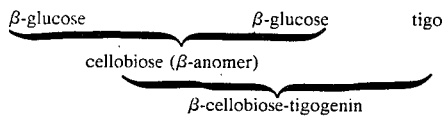

Glucosides having tigogenin and diosgenin aglycones were synthesized and tested according to the following procedures.

EXAMPLE 1

Synthesis

A series of saponins were synthesized by glycosylation of the hydroxyl group of the two sapogenins, tigogenin ($5\alpha,20\alpha,22\alpha,25D$-spirostan-$3\beta$-ol) and diosgenin ($5\alpha,20\alpha,22\alpha,25D$-spirosten-$3\beta$-ol). Synthesis of the saponins was accomplished with a modified version of the method described by Rosevear at al., "Alkyl Glycoside Detergents" A Simpler Synthesis and Their Effects on Kinetic and Physical Properties of Cytochrome C Oxidase." *Biochemistry*, 19:4108–4115, 1980.

a. Weigh 1 mmol (678 mg) of cellobiose octoacetate ($\beta$-anomer) or 1 mmol (390 mg) of glucose pentaacetate ($\beta$-anomer) into a foil-covered reaction vessel. While stirring magnetically, add 5 ml of glacial acetic acid and stir for a few minutes. Quickly add 5 ml of 31% HBr in glacial acetic acid. Immediately shut in the fumes with a stopper and stir vigorously for 45 to 55 min (cellobiose) or 30 to 40 min (glucose).

b. Add 10 ml of choloform for cellobiose or dichloromethane for glucose. Pour into a separating funnel containing 30 ml of ice and water. Shake for 2 min and extract the bottom nonaqueous layer into 30 ml of a cold saturated sodium bicarbonate solution previously saturated with chloroform or dichlormethane. Shake for 2 min. Repeat $NaHCO_3$ extraction twice or until the pH of the aqueous layer is >7.0. Wash the nonaqueous phase three times with cold solvent-saturated distilled water.

c. Dry the extracted solvent layer over 500 mg. of magnesium sulfate while stirring for 30 min. Centrifuge and wash the precipitate with dry solvent.

d. Pour the dried filtrate into a foil-covered, 50-ml screw-cap tube and evaporate to about 10 ml with $N_2$ at low heat.

e. Keeping the reaction vessel protected from light and air moisture as much as possible, add: 1 mmol of tigogenin or diosgenin; 200 mg of dry silver carbonate; one small iodine crystal; and 1 g of 4 Å molecular sieves. Stir in the dark for 12 to 24 h.

f. Centrifuge at a low speed for 10 min. and transfer the supernatant to a foil-covered, 50-ml screw-cap tube. Wash the precipitate twice with 5 ml of solvent and combine the solvents.

g. Evaporate the combined solvent with $N_2$ to a cloudy syrup of about 1 to 2 ml. Add a stir bar and 10 ml of a solution of triethylamine:methanol:water (1:2:1). Stir for 30 min. and let stand overnight.

h. Transfer the solution quantitatively into dialyzing tubing with 40 ml of water. Dialyze it against tap water for 48 h.

i. Transfer the solution to a container for freeze-drying. Evaporate the water overnight.

j. Dissolve the resulting white powder in dichloromethane-methanol (10:1, vol/vol) and transfer to a chromatography column filled with silica gel type 60 (230-400 mesh, E. Merck Reagents). Separate 7 ml fractions with the above solvent and after 150 ml, use methanol to elute the saponins.

k. Perform thin-layer chromatography (TLC) on a small amount (around 10 $\mu$g) with chloroform:methanol:water (65:38:10) as the solvent. Use a Cu acetate solution for charring. Saponins typically have retardation factor ($R_f$) values around 0.6 to 0.8 and give a bluish or brownish color.

This procedure probably synthesized saponins with $\beta$-glycosidic bonds, or, in the case of cellobiose, a mixture of $\beta$- and $\alpha$-glycosides. It was possible to synthesize the $\alpha$-isomer, by using glucose pentaacetate ($\alpha$-anomer) and $ZnCl_2$ instead of $AgCO_3$ as catalyst.

Glucosides having tigogenin and diosgenin aglycones were tested for in vitro binding of cholesterol according to the following procedure:

EXAMPLE 2

In Vitro Binding of Cholesterol a. Prepare a micellar suspension of cholesterol by placing in a flask caprylic acid ($1.2 \times 10^{-3}$M), glyceryl monoleate ($0.6 \times 10^{-3}$M), and [4-$^{14}$C] cholesterol ($0.3 \times 10^{-3}$M; specific activity ~25,000 dpm/mg), and agitating these for 1 h at 38° C. with sodium taurocholate ($10 \times 10^{-3}$M) in 0.1M phosphate buffer, pH 6.2 (20). The suspension contains approximately 58 $\mu$g of cholesterol/ml. Centrifuge the suspension at 10,000 rpm for 30 min. before use.

b. Place 100 $\mu$g of the synthetic saponin dissolved in methanol in a 50-ml screw-cap tube and evaporate the solvent under $N_2$ in a warm-water bath.

c. Add 4 ml of the micellar suspension and shake it for 2 h at room temperature.

d. Transfer the medium to centrifuge tubes. Centrifuge at 3,000 rpm for 20 min.

e. Determine the radioactivity in 0.5 ml of the upper solvent phase with 10 ml of toluene-based scintillation fluid.

f. Treat blanks as above without adding the synthetic saponin.

Results of these tests showed that binding of cholesterol occurs with the synthetic saponins. Representative data from the test appears in Table III:

TABLE III

| In Vitro Binding of Cholesterol by Synthetic Saponins[a] | | |
|---|---|---|
| Saponin | Mass/flask ($\mu$g) | Cholesterol bound ($\mu$g) |
| None[b] | 0 | 0 |
| Cellobiose-tigogenin[b] | 250 | 21 |
| Cellobiose-tigogenin[b] | 500 | 37 |
| Cellobiose-tigogenin[b] | 750 | 46 |
| Cellobiose-tigogenin[b] | 1000 | 60 |
| Cellobiose-diosgenin[b] | 1000 | 26 |
| Glucose-diosgenin[c] | 1000 | 49 |
| Glucose-tigogenin[c] | 1000 | 40 |

[a]Results are average of three determinations.
[b]Mixture of $\alpha$- and $\beta$-glycosides.
[c]Mainly $\beta$-glycoside.

Further experimentation was conducted to determine the effect of the synthesized saponins on living animals.

EXAMPLE 3

Effects of Synthetic Glycosides in Vivo

Effects of the synthetic glycosides on the intestinal absorption of cholesterol in rats were tested according to the procedure of M. R. Malinow, et al., "Effect of Alfalfa Saponins on Intestinal Cholesterol Absorption in Rats." *Am. J. Clin. Nutr.* 30:2061-2067, 1977. The animals were fed semipurified cholesterol-free food from 8 a.m. to 10 a.m. for ten days. On the day of the experiment, the rats were anesthetized at about 10:30 a.m. and the test substance, as well as a pulse dose of radioactive cholesterol, were given per gastric tube. The excretion of $^{14}C$-neutral steroids was determined in feces collected for 72 h after intragastric administration of the test substances and 2 mg of [4-$^{14}C$] cholesterol (specific activity ~0.25 $\mu$Ci/mg).

As shown in Table IV, these rate experiments demonstrated that the synthetic glycosides inhibit the intestinal absorption of cholesterol. No significant inhibition was observed with sapogenins. Better results were obtained with a longer sugar moiety (cellobiose) than with a shorter moiety (glucose).

TABLE IV

Effects of Sapogenins and Synthetic Glycosides on Cholesterol Absorption in Rats[a]

| Series | Substance administered | Number of rats | Weight (g) | Dose (mg/rat) | Intestinal Absorption of cholesterol (I.D.) | Student's t test, P versus controls | Relative Absorption |
|---|---|---|---|---|---|---|---|
| I | none | 6 | 242 ± 3 | 0 | 74.6 ± 2.3 |  | 100 |
|  | glucose-tigogenin | 6 | 246 ± 7 | 14 | 46.2 ± 1.8 | <0.001 | 62 |
|  | glucose-diosgenin | 6 | 245 ± 5 | 14 | 52.6 ± 3.7 | <0.001 | 71 |
|  | alfalfa extract | 6 | 249 ± 9 | 14 | 60.2 ± 3.7 | <0.01 | 81 |
| II | none | 6 | 290 ± 7 | 0 | 74.8 ± 1.6 |  | 100 |
|  | cellobiose-tigogenin | 6 | 291 ± 12 | 14 | 39.6 ± 1.8 | <0.001 | 53 |
|  | cellobiose-diosgenin | 6 | 287 ± 4 | 14 | 53.7 ± 1.3 | <0.001 | 72 |
|  | alfalfa extract | 6 | 275 ± 8 | 14 | 56.3 ± 1.1 | <0.01 | 75 |
| III | none | 6 | 268 ± 5 | 0 | 78.0 ± 2.1 |  | 100 |
|  | tigogenin | 6 | 259 ± 5 | 15 | 80.4 ± 1.4 | N.S. | 103 |
| IV | none | 6 | 328 ± 4 | 0 | 73.5 ± 2.0 |  | 100 |
|  | diosgenin | 6 | 330 ± 4 | 15 | 76.4 ± 2.6 | N.S. | 104 |
| V | none | 6 | 276 ± 7 | 0 | 77.7 ± 2.2 |  | 100 |
|  | cellobiose-cholesterol | 6 | 282 ± 3 | 15 | 69.5 ± 1.3 | 0.01 | 89 |
|  | glucose-cholesterol | 6 | 273 ± 8 | 15 | 72.5 ± 1.0 | N.S. | 93 |
|  | alfalfa extract | 6 | 277 ± 5 | 15 | 68.4 ± 2.3 | 0.02 | 88 |

Values are mean ± SE. Abbreviations: I.D., injected dose; N.S., not significant.
[a]The excretion of $^{14}C$-neutral steroids was determined in feces collected for 72 h after intragastric administration of glycosides or sapogenins and 2 mg of [4-$^{14}C$]-cholesterol.

The mechanism whereby cholesterol absorption is inhibited by sapogenin and sterol compounds is unknown. However, it is possible that the compounds form an insoluble complex with cholesterol in the intestinal lumen and thereby prevent the absorption of dietary cholesterol. Additionally, the compounds may bind biliary cholesterol and cholesterol from desquamated intestinal cells and, thus, may induce negative cholesterol balance through the increased excretion of endogenous cholesterol.

In the above described experiments, synthetic sapogenin and sterol compounds inhibited the absorption of exogenous cholesterol in laboratory animals. It is thus anticipated that they will also be effective in preventing atherosclerosis or inducing its regression without toxic effects. It is an advantage that such synthetic compounds are pure substances with known or determinable chemical structures and may be synthesized in sufficient purity so as to be used to treat human beings. As indicated by their ability to prevent the absorption of cholesterol, synthetic sapogenin and sterol compounds may reduce deaths due to atherosclerotic disease, a most significant cause of death in the adult population of the Western world.

Having given examples of preferred embodiments of my invention, it will be apparent to those skilled in the art that changes and modifications may be made without departing from my invention in its broader aspects. I therefore intend the appended claims to cover all such changes and modifications as fall within the true spirit and scope of my invention.

I claim:

1. A method of treating a human or other warm-blooded animal subject to reduce digestive absorption of cholesterol, the method comprising administering to the subject an effective amount of a nontoxic, substantially pure, synthetic, glycosidic compound selected from the group consisting of glycosides having tigogenin aglycones.

2. The method of claim 1 wherein the glycoside is a glucoside.

3. The method of claim 2 wherein the glycoside is a glucose-tigogenin.

4. The method of claim 2 wherein the glycoside is a cellobiose-tigogenin.

5. The method of claim 4 wherein the glycoside is a $\beta$-cellobiose-tigogenin.

6. The method of claim 1 wherein the glycoside is administered orally.

7. A method of treating a human or other warm-blooded animal subject to reduce digestive absorption of cholesterol, the method comprising administering an effective amount of a nontoxic cholesterol glycoside to the subject.

8. A method of treating a human or other warm-blooded animal subject to reduce digestive absorption of cholesterol, the method comprising administering to the subject an effective amount of a glucose-cholesterol.

9. The method of claim 8 wherein the glucose-cholesterol is a cellobiose-cholesterol.

10. The method of claim 9 wherein the glucose-cholesterol is a $\beta$-cellobiose-cholesterol.

11. The method of claim 7 wherein the cholesterol glycoside is administered orally.

12. The method of claim 1 wherein the glycoside consists of a carbohydrate bonded to the aglycone by a $\beta$-oriented glycosidic bond.

13. A method of treating a human or other warm-blooded animal subject to reduce digestive absorption of cholesterol, the method comprising administering to the subject an effective amount of an ester selected from the group consisting of diosgenin maleate, tigogenin maleate, and mixtures thereof.

14. The method of claim 8 wherein the glucose-cholesterol is administered orally.

15. A method of treating a human or other warm-blooded animal subject to reduce digestive absorption of cholesterol, the method comprising administering to the subject an effective amount of cholesterol maleate.

* * * * *